(12) United States Patent
DeCarlo et al.

(10) Patent No.: US 8,735,571 B2
(45) Date of Patent: May 27, 2014

(54) COMPOSITION, PREPARATION, AND USE OF DENSE CHITOSAN MEMBRANE MATERIALS

(75) Inventors: Arthur A. DeCarlo, Vestavia Hills, AL (US); April Ellis, Pinson, AL (US); Thomas P. Dooley, Pinson, AL (US); Maria Belousova, Birmingham, AL (US)

(73) Assignee: Agenta Biotechnologies, Inc., Birmingham, AL (US)

( * ) Notice: Subject to any disclaimer, the term of this patent is extended or adjusted under 35 U.S.C. 154(b) by 93 days.

(21) Appl. No.: 13/334,388

(22) Filed: Dec. 22, 2011

(65) Prior Publication Data

US 2013/0164311 A1    Jun. 27, 2013

(51) Int. Cl.
  *C08B 37/00*    (2006.01)
  *C07H 5/04*    (2006.01)
  *C07H 5/06*    (2006.01)

(52) U.S. Cl.
  USPC ........................................................ 536/55.3

(58) Field of Classification Search
  None
  See application file for complete search history.

(56) References Cited

U.S. PATENT DOCUMENTS

| | | | |
|---|---|---|---|
| 4,401,807 A * | 8/1983 | Koshugi | 536/20 |
| 7,195,675 B2 * | 3/2007 | Okazaki et al. | 127/29 |
| 7,371,403 B2 * | 5/2008 | McCarthy et al. | 424/445 |

* cited by examiner

*Primary Examiner* — Layla Bland
(74) *Attorney, Agent, or Firm* — Thomas G. Peterson; Bradley Arant Boult Cummings LLP

(57) ABSTRACT

A composition of exceptionally dense chitosan and a novel method for producing the dense chitosan structure have been described. The novel production method employs coincident compression and vacuum on a neutralized chitosan polymer that results in an exceptionally dense chitosan film or membrane material. The dense chitosan film or membrane composition possesses multiple physical and clinically appealing qualities for a variety of medical applications on or in animals, mammals, or humans.

3 Claims, No Drawings

COMPOSITION, PREPARATION, AND USE OF DENSE CHITOSAN MEMBRANE MATERIALS

FIELD OF DISCLOSURE

The present invention relates to dense chitosan film or membrane materials and methods for their preparation. The materials have utility in medical, scientific, and other industries.

BACKGROUND

Functional biomaterial research has been directed toward the development of improved scaffolds for wound healing and tissue engineering. A number of biodegradable polymers have been explored as scaffolds for wound healing and tissue engineering applications and include synthetic polymers like poly-caprolactone, poly(lactic-co-glycolic acid), poly(ethylene glycol), and natural polymers such as alginate, gelatin, collagen, starch, and chitosan. Among them, naturally derived polymers are of special interest due to, as natural components of living structures, their biological and chemical similarities to natural tissues. In this context, chitosan has been found as a fascinating candidate in a broad spectrum of applications along with unique biological properties including biocompatibility, biodegradability to harmless saccharide products, nontoxicity, physiological inertness, remarkable affinity to proteins, in addition to antibacterial, antifungal, and haemostatic properties.

The recorded use of chitosan dates back to the 19th century, when Rouget discussed the deacetylated form of chitosan in 1859. Chitin, the source material for chitosan, is one of the most abundant organic materials, being second only to cellulose in the amount produced annually by biosynthesis. It is an important constituent of the exoskeleton in animals, especially in crustaceans, molluscs and insects. It is also the principal fibrillar polymer in the cell wall of certain fungi, and can be produced by microalgae. Deacetylated chitin derivatives have been referred to as "chitosan". When these two terms were first used in the 1800's, it was believed that chitin and chitosan always occurred in nature as distinct, well-defined, unique, and invariant chemical species, with chitin being fully acetylated and chitosan being fully deacetylated compositions. It was approximately a century later, however, before it was discovered that the terms "chitin" and "chitosan" are, in fact, ambiguous. Rather than referring to well-defined compounds, these terms actually refer to a family of compounds that exhibit widely differing physical and chemical properties. These differences are due to the products' varying molecular weights and varying degrees of acetylation.

Chitosan is a linear polysaccharide, composed of glucosamine and N-acetyl glucosamine units linked by $\beta$ (1-4) glycosidic bonds—in essence, strings of sugar units. Depending on the source and preparation procedure, its molecular weight generally ranges from 10 kDa to over 1000 kDa. The molecular weight of the chitosan polymer is routinely determined by viscosity and is expressed in terms of Centipoise (CPS) or Millipascal (mPas) units, and can range from about 5 mPas to 3000 mPas. The content of glucosamine is termed as the degree of deacetylation (DD), and can range from 30% to 95%. In its crystalline form, chitosan is normally insoluble in aqueous solution above pH 7, however, in dilute acids (pH 6.0), the protonated free amino groups on glucosamine facilitate solubility of the molecule (Kim, Seo et al. 2008). Generally, chitosan has three types of reactive functional groups, an amino group as well as both primary and secondary hydroxyl groups at the C(2), C(3), and C(6) positions, respectively. These groups allow modification of chitosan for specific applications, which can produce various useful scaffolds for tissue engineering applications. The chemical nature of chitosan in turn provides many possibilities for covalent and ionic modifications which allow extensive adjustment of mechanical and biological properties.

Chitin Processing

As mentioned above, chitin is present within numerous taxonomic groups. However, commercial chitins are usually isolated from marine crustaceans, such as shrimp. Crustacean shells consist of 30-40% proteins, 30-50% calcium carbonate, and 20-30% chitin and also contain pigments of a lipidic nature such as carotenoids (astaxanthin, astathin, canthaxanthin, lutein and $\beta$-carotene). These proportions vary with species and with season.

When chitin is extracted by acid treatment to dissolve the calcium carbonate followed by alkaline extraction to denature and dissolve the proteins and by a depigmentation step, a colorless to off-white product is obtained mainly by removing the astaxanthin. The preparation method is a factor that affects the sample characteristics. Early studies have clearly demonstrated that specific characteristics of these products (Mw, DD) depend on the process conditions. Typically, however, commercial chitins are prepared by a first step of deproteinisation followed by a second step of demineralization. In these conditions a "collapsed chitin", in which the native structure of the chitin is lost, is extracted. On the other hand, "compacted chitin", in which the native chain and fibrous structures are intact and stabilized, is extracted when demineralization occurred in the first step. Chitosan prepared by either method of chitosan extraction apply to the present invention. Furthermore, the present invention does not restrict the source of chitosan from natural, semi-synthetic, or synthetic sources.

Chitin Deacetylation to Chitosan

Chitosan is prepared by hydrolysis of the acetamide groups of chitin. This is normally conducted by harsh alkaline hydrolysis treatment due to the resistance of such groups imposed by the trans arrangement of the C2-C3 substituents in the sugar ring (Horton and Lineback 1965).Thermal treatments of chitin under strong aqueous alkali are usually needed to give partially deacetylated chitin (DD higher than 70%), regarded as chitosan. Usually, sodium or potassium hydroxides are used at a concentration of 30-50% w/v at high temperature (100° C.). This harsh hydroxide/heat method has the coincident effect of reducing or removing potential bacterial endotoxins, which is beneficial for biomedical applications of the resulting chitosan materials.

Chitosan DD can range from 56%-99% depending on chitin source and methods of chitosan preparation (Abou-Shoer 2010). Factors that affect the extent of deacetylation include concentration of the alkali, previous treatment, particle size and density of chitin. In practice, the maximal DD that can be achieved in a single alkaline treatment is about 75-85% (Roberts 1998). In general, during deacetylation, conditions must be the proper ones to deacetylate, in a reasonable time, the chitin to yield a chitosan that is (subsequently) soluble in diluted acetic acid. It has become evident that the overriding factor regarding the fine structure of chitosan is the chemical polydispersion of the DD value (Roberts 1998). During chitosan deacetylation, the degradation of the polymeric chain takes place. Chitosan scaffolds with low DD (75-85%) displayed a more regular structure and the pores were fairly uniform and parallel with a polygonal cross section (Tigli and Gumusderelioglu 2008). The lateral pore connectivity was much lower than for scaffolds with high deacetylation degrees (>85%). Swelling studies were also performed but no relationship was found between DD and swelling ratio. Mechanical testing of chitosan scaffolds showed that mechanical strength was higher with higher DD. Biodegradability of the scaffolds also depends on the DD.

Chitosan Depolymerization

The main limitations in the use of chitosan in certain applications are its high viscosity and low solubility at neutral pH. Low Mw chitosans and oligomers can be prepared by hydrolysis of the polymer chains. For some specific applications, these smaller molecules have been found to be much more useful. Chitosan depolymerization can be carried out chemically, enzymatically, or physically. Chemical depolymerization is mainly carried out by acid hydrolysis using HCl or by oxidative reaction using $HNO_2$ and $H_2O_2$. It has been found to be specific in the sense that $HNO_2$ attacks the amino group of deacetylated glucosamine units, with subsequent cleavage of the adjacent glycosidic linkage (Prashanth and Tharanathan 2007). In the case of enzymatic depolymerization, low molecular weight chitosan with high water solubility were produced by several enzymes such as chitinase, chitosanase, gluconase and some proteases. Non-specific enzymes including lysozyme, cellulase, lipase, amylase and pectinase that are capable of depolymerizing chitosan are known. In this way, regioselective depolymerization under mild conditions is allowed (Aranaz, Mengibar et al. 2009).

There is no correlation between the Mw of chitosan and its swelling behavior (Roldo, Hornof et al. 2004; El-Kamel, Ashri et al. 2007). The tensile strength (TS), the percentage elongation at break (% EB) and the elastic modulus (EM) are important parameters to indicate the strength and elasticity of a film. ASTM International standard test methods have been established for the evaluation of the physical parameters for thin films or membranes (ASTM 2002; ASTM 2006). Medium Mw chitosan films have the highest values for TS and EM, followed by high Mw and low Mw chitosan films (El-Kamel, Ashri et al. 2007). On the other hand, the highest % EB is obtained for low Mw chitosan films, followed by high and medium Mw chitosan films.

Effect of Pore Variations

The mechanical properties of chitosan-based scaffolds are dependent on the pore sizes and pore orientations. Chitosan can be formed as interconnected-porous structures by freezing and lyophilizing a chitosan solution or by processes such as an "internal bubbling process (IBP)" where $CaCO_3$ is added to chitosan solutions to generate chitosan—$CaCO_3$ gels in specific shapes by using suitable molds (Chow and Khor 2000). Tensile testing of hydrated samples shows that porous chitosan membranes have greatly reduced elastic moduli (0.1-0.5 MPa, wherein a megapascal unit=$N/mm^2$) compared to non-porous chitosan membranes (5-7 MPa). The extensibility (maximum strain) of porous membranes varied from values similar to nonporous chitosan (approximately 30%) to greater than 100% as a function of both pore size and orientation. Porous membranes exhibited a stress-strain curve typical of composite materials with two distinct regions: a low-modulus region at low strains and a transition to a 2-3 fold higher modulus at high strains. The tensile strengths of these porous structures are reportedly in the range of 30-60 kPa (Madihally and Matthew 1999).

Chen and Hwa reported effects of the molecular weight of used chitosans and their crystallinity on the mechanical property of chitosan membrane (Chen and Hwa 1996). That is, the lower molecular weight of chitosan used, the lower the tensile strength of the chitosan membrane prepared due to the chance of entanglement differences. In other words, the use of lower molecular weight chitosan produces less entanglement. Crystallinity difference of chitosan may be attributed to another factor. The lower the molecular weight of chitosan used, the lower the enthalpy of the resulting membrane. These implied that the lower tensile strength of the membrane was a result of less crystallinity in the chitosan membrane prepared from low molecular weight of chitosan.

Biodegradability

Chitosan is absent from mammals but can be degraded in vivo by several enzymes, most notably lysozyme, chitinase, and NAGase (Dalian, da Luz Moreira et al. 2007; Kim, Seo et al. 2008) (Aranaz, Mengibar et al. 2009) (Niekraszewicz 2005). Biodegradation leads to the release of non-toxic oligosaccharides of variable length which can be subsequently incorporated into glycosaminoglycans and glycoproteins, to metabolic pathways, or be excreted. Lysozyme, a non-specific glycoside hydrolase present in mammalian tissues and implicated in innate immunity, seems to play a significant degradation role on chitin and chitosan. The degradation kinetics seem to be inversely related to the degree of crystallinity, which is controlled mainly by the DD. Moreover, the distribution of acetyl groups also affects biodegradability since the absence of acetyl groups or their homogeneous distribution (random rather than block) results in very tow rates of enzymatic degradation.

Finally, several studies reported that the length of the chains (Mw) also affects the degradation rate. The understanding and control of the degradation rate of chitosan-based materials and medical devices is of great interest since degradation is essential in many small and large molecule release applications and in functional tissue regeneration applications. In certain uses, the rate of scaffold degradation should mirror the rate of new tissue formation or be adequate for the controlled release of bioactive molecules (e.g., natural compounds, pharmaceuticals, biologics, nucleic acids, vaccines, and immune effectors). Thus, it is important to understand and control both the mechanism and the rate by which each material is degraded.

The degradation rate also affects the biocompatibility since very fast rates of degradation liberate (and potentially accumulate) the amino sugars that can produce a mild inflammatory response. Chitosan samples with tow DD induce a more acute inflammatory response while chitosan samples with high DD induce a minimal response due to the low degradation rate. Degradation has been shown to increase as DD decreases. In other words, in general, degradation is enhanced by increased acetylation (Lim, Song et al. 2008). Kofuji et al. investigated the enzymatic behaviors of various chitosans by observing changes in the viscosity of chitosan solution in the presence of lysozyme (Kofuji, Qian et al. 2005). They found that chitosan with a low DD tended to be degraded more rapidly. However, other authors reported that differences in degradation are due to variations in the distribution of acetamide groups in the chitosan molecule. This occurs due to differences in deacetylation conditions which influences viscosity of the chitosan solution by changing the inter- or intramolecular repulsion forces. Therefore, it can be concluded that it is impossible to estimate biodegradation rate from the DD alone.

Biocompatibility

Chitosan shows very good biocompatibility, but this property depends on the characteristics of the sample (e.g., natural source, method of preparation, Mw and DD). Although the digestive (oral/gastrointestinal) enzymes can partially degrade chitosan, when orally administered it is not absorbed. For this reason, chitosan is considered as not bioavailable by the oral route. Chitosan has a LD50 in mice of around 16 g/kg, a very high dose and consistent with negligible acute toxicity. Toxicity of chitosan is reported to depend on DD. Schipper et al. reported that chitosans with DD higher than 35% showed low toxicity, while a DD under 35% chitin) caused dose-dependant toxicity (Schipper, Varum et al. 1996). On the other hand, Mw of chitosan did not influence toxicity (Schipper, Varum et al. 1996).

The cytocompatibility of chitosan has been proven in vitro with myocardial, endothelial and epithelial cells, fibroblasts, hepatocytes, chondrocytes, and keratinocytes (Aranaz, Mengibar et al. 2009). This property seems to be related to the DD of the samples. When the positive charge of the polymer increases, the interactions between chitosan and the cells increase too, due to the presence of free amino groups. The adhesion and proliferation of keratinocytes and fibroblasts on several chitosan films with different DDs depend on both, DD and cell type. In both cells, the percentage of cell adhesion was strongly dependent on the DD, increasing with this parameter. The type of cell was a factor that also affected the adhesion, being more favorable for fibroblasts, which exhibit a more negative charge surface than for keratinocytes. On the other hand, the proliferation decreased considerably by increasing the DD. Therefore, a balance of cell adhesion and cell proliferation in wound healing and biological application requires an appropriate DD.

Chitosan films containing different Mw chitosans had different forces of adhesion but statistical analysis revealed that there was no significant difference in bioadhesion force between the films. On the contrary, Roldo et al. showed that the maximal detachment force of medium Mw chitosan was higher than that of both tow and high Mw chitosans (Roldo, Hornof et al. 2004).

Impure chitin and chitosan with residual proteins could cause allergic reactions such as hypersensitivity within some individuals. The protein content in a sample depends on the source of the sample and, especially, on the method of preparation. When prepared as described above (e.g., acid followed by strong base plus heat), purified chitosan is non-allergenic. While 0.2-0.3 percent of the human population exhibits allergies to marine crustaceans (Osterballe, Hansen et al. 2005; Osterballe, Mortz et al. 2009), the following conclusions were drawn from a respected authority on chitosan, Dr. Riccardo Muzzarelli:

It is presently unwise to interpret chitin as an allergenic substance, more clinical and genetic research being needed. Crab, shrimp, prawn and lobster chitins, as well as chitosans of all grades, once purified, should not be considered as "crustacean derivatives" because the isolation procedures have removed proteins, fats and other contaminants to such an extent as to permit to classify them as chemicals regardless of their origin. [(Muzzarelli 2010) p. 305]

The major shrimp allergen has been identified as the muscle protein tropomyosin . . . . Shrimp-derived glucosamine is safe even for individuals hypersensitive to tropomyosin. Villacis et al. state that glucosamine supplements from various manufacturers to not contain clinically relevant levels of allergens [76]. Gray et al. clearly state that "shellfish allergy is caused by IgE antibodies to antigens in the flesh of the shellfish and not the shell; therefore it should be safe for patients with shellfish allergy to take glucosamine supplement" [77]. [(Muzzarelli 2010) p. 300]

Furthermore, with regard to purified chitosan as a material within "wound dressing" products, Dr. Muzzarelli states:

"In experimental and pre-clinical surgical trials, the use of chitin/chitosan and their derivatives has never led to allergies or other diseases." [(Muzzarelli 2010) p. 304]

Haemostatic Considerations

Chitosan Mw also affects the binding or agglutination of red blood cells Shyu et al. 2001; Ishihara, Obara et al. 2006; Pang, Chen et al. 2007; Aranaz, Mengibar et al. 2009; Zhang, Xia et al. 2010). In a recent paper, a comparative study has been carried out among solid-state chitosan and chitosan acetic acid physiological saline solution (Jian, Feng et al. 2008). Several chitosan samples with Mw from 2000 to 400 kDa and DD from 90 to 70% were tested. It was found that solid-state chitosan and "chitosan acetic acid physiological saline solution" followed different haemostatic mechanisms. When blood was mixed with chitosan acetic acid physiological saline solution, the erythrocytes aggregated and they were deformed. The DD, especially a high DD, in the chitosan acetic acid physiological saline solution, had a significant effect on the unusual aggregation and deformation of erythrocytes, compared with the effect of Mw within a range between 100-1,000 kDa. However, this phenomenon could not be observed in solid-state chitosan. Solid-state chitosan with a high DD bound more platelets and was more haemostatic.

Numerous commercial medical device products containing chitosan and its salt forms are available for use in controlling hemorrhage (e.g., acidic lyophilized chitosan sponges). These devices are typically applied to the exterior surfaces of wounds as wound dressings or "bandages" (see below re: FDA Approved Devices)

Mucoadhesion

Several factors affect chitosan mucoadhesion, such as physiological variables and the physicochemical properties of chitosan. The mucus is composed of a glycoprotein called mucin, which is rich in negative charges since it has sialic acid residues. In the stomach, chitosan is positively charged due to the acidic environment and, therefore, it can interact with mucin by electrostatic forces. The extent of this union depends on the amount of sialic acid present in the mucin and on the Mw and DD of chitosan. It has been found that when the Mw of chitosan increases, the penetration in the mucin layer also increases and hence the mucoadhesion is stronger (Lehr, Bouwstra et al. 1992). On the other hand, a higher DD leads to an increase in charge density of the molecule and the adhesive properties become more relevant (He, Davis et al. 1998).

Antimicrobial Activity

One of the inherent properties of chitosan is that it confers considerable antibacterial activity against a broad spectrum of bacteria (No, Park et al. 2002; Jou, Yuan et al. 2007). Aimin et al. (Aimin, Chunlin et al. 1999) has shown that chitosan can reduce the infection rate of experimentally induced osteomyelitis by *Staphylococcus aureus* in rabbits. This is related to the cationic nature of chitosan by amino groups and to anions on the bacterial cell wall. The interaction between positively charged chitosan and negatively charged microbial cell wall leads to the leakage of intracellular constituents. The binding of chitosan with DNA and inhibition of mRNA synthesis occurs via the penetration of chitosan into the cytosol of the microorganisms and interfering with the synthesis of mRNA and proteins (Liu, Guan et al. 2001).

Other mechanisms have also been proposed. Chitosan may inhibit microbial growth by acting as a chelating agent rendering metals, trace elements or essential nutrients unavailable for the organism to grow at the normal rate. Chitosan is also able to interact with flocculate proteins, but this action is highly pH-dependent.

In addition, chitosan has antifungal properties. Several authors have proposed that the antimicrobial action of chitosan against filamentous fungi could be explained by a more direct disturbance of membrane function. However, it is not clear whether the antimicrobial activity of chitosan is caused by growth inhibition (fungistatic) or cell death (fungicidal).

Antioxidant Activity

Chitosan has shown a significant scavenging capacity against different radical species, the results being comparable to those obtained with commercial antioxidants. Samples prepared from crab shell chitin with DD of 90, 75, and 50% where evaluated on the basis of their abilities to scavenge 1,1-diphenyl-2-picrylhydrazyl (DPPH), hydroxyl, superoxide, and alkyl radicals. The results revealed that chitosan with higher DD exhibited the highest scavenging activity (Park, Je et al. 2004). On the other hand, chitosans of different size as well as their sulfate derivatives, were assayed against superoxide and hydroxyl radicals. A negative correlation was found between chitosan Mw and activity. The chitosan sulfated derivatives presented a stronger scavenging effect on peroxide radicals but the chitosan of lowest Mw showed more considerable ferrous ion-chelating potency than others. The chelation of metal ions is one of the reasons why chitosan may be considered as a potential natural antioxidant. Chitosans may retard lipid oxidation by chelating ferrous ions present in the system, thus eliminating their pro-oxidant activity or their conversion to ferric ion (Peng 1998).

Current Uses of Chitosan

Chitosan, a natural cationic polysaccharide and salt forms thereof (e.g., -acetate, -lactate, -chloride, -phosphate, etc.) have received considerable attentions as a nontoxic and biodegradable biopolymer for diverse applications, especially in foods, medical devices, cosmetics and hair care products, and pharmaceutics (Johnson and Nichols 2000).

With regard to foods, in recent years chitosan was made available over the counter as a dietary supplement or cholesterol-lowering agent in multiple nutritional supplement products due to its ability to bind fat. Chitosans have been identified as versatile biopolymers of natural origin for food preservation due to their antimicrobial action against food spoilage microorganisms and antioxidant properties. The pH-dependent solubility allows them to be formed into various shapes (e.g., beads, films and membranes) using aqueous processing. Beads and particles have been described for use in resins, fillers, absorbants, adsorbants, and insulation (Smith 1994) (Unger and Rohrbach 1996). The use of chitosan coating as a protective barrier to extend the storability of many fruits and vegetables has been widely documented.

Current Medical Uses of Chitosan Structures

Due to its biological properties, chitosan has been employed in research and/or commercial products in wound healing management (e.g., wound dressings and "bandages"), implantable device systems such as orthopedic and periodontal composites, scaffolds for tissue regeneration, and drug- and DNA-delivery systems.

Chitosan, as a biodegradable natural biopolymer, has served as a biocompatible wound dressing for many years. Chitosan-based materials are highly biocompatible without toxicity and with only an early, mild, macrophage-dominated inflammatory response. In general, the unique chemical and biological properties, biodegradation characteristics, and biocompatibility of chitosan make it attractive in biomedical applications. Chitosan-containing products are currently available on the medical market, typically as US FDA Class I medical device wound dressings or "bandages" to promote wound healing. Chitosan-based products have been used perhaps even more extensively internationally than in the United States.

Purified Chitosan Safety in Humans

The safety of purified chitosan in humans has been widely reported (Illum 1998; Baldrick 2010). Safety in humans has been demonstrated in various contexts:

1. FDA Approved Devices:

Purified chitosan is a component in multiple US FDA-approved Class I medical and dental devices, and in most cases as the principal component. It has been used in various finished product forms, such as granules, a film component of bandages and gauze, and a lyophilized "sponge". Examples of FDA 510(k) Premarket Notification cleared Class I products include HemCon Bandage, HemCon Dental Dressing, HemoHalt Hemostasis Pad Wound Dressing, Aquanova Super-Absorbent Dressing, CELOX Topical Hemostatic Granules in Soluble Bag, and ChitoGauze.

2. GRAS Food Additive:

Chitosan is considered as Generally Accepted as Safe (GRAS) as a food additive at the level of "self-affirmed" by various manufacturers of chitosan (e.g., Primex). To the best of our knowledge, a GRAS designation at the higher level of "no comment" following a full FDA review has not yet occurred. Chitosan is considered by the scientific community to be safe for use in foods, albeit with one caveat—ingested chitosan has affinity for dietary lipids and can reduce lipid uptake from the gastrointestinal tract.

3. Cosmetic & Consumer Skincare Products:

Chitosan is listed among the International Nomenclature of Cosmetic Ingredients (INCI). Chitosan and its various salt forms (e.g., lactate, glycolate, ascorbate, formate, & salicylate) and other organic derivatives are listed as ingredients for use in cosmetics and consumer skincare products, and via multiple vendors. However, chitosan has not yet undergone an evaluation by the Cosmetics Ingredients Review (CIR). This panel of industry experts evaluates a very limited number of cosmetic ingredients for safety. To the best of our knowledge, chitosan has not warranted consideration by the expert panel, and is considered by the scientific community as safe for use in consumer skincare and cosmetic products.

Tissue Engineering

Tissue engineering is a multidisciplinary science, including fundamental principles from materials engineering and molecular/cellular biology in efforts to develop biological substitutes for failing tissues and organs. In the most general sense, tissue engineering seeks to fabricate living replacement parts for the body. Langer and Vacanti (Langer and Vacanti 1993) reported that the most common approach for engineering biological substitutes is based on living signal molecules, and polymer scaffolds. The cells synthesize matrices of new tissue as well as function on behalf of the diseased or damaged tissues, while the scaffold provides the suitable environment for the cells to be able to effectively accomplish their missions such as adherence, proliferation, and differentiation. The function of the signal molecules is to facilitate and promote the cells to regenerate new tissue. The scaffolds provide not only temporary three-dimensional frameworks to form the designed tissues, but also space filling and controlled release of bioactive signal molecules. To perform these varied functions in tissue engineering, scaffold should meet the following requirements: (1) biocompatibility with the tissues, and an environment that promotes cellular adhesion, (2) biodegradability at the optimal rate corresponding to the rate of new tissue formation, (3) nontoxicity and non-immunogenicity, (4) optimal mechanical properties, and (5) adequate porosity and morphology for transporting of gases, metabolites, nutrients and signal molecules both within the scaffold and between the scaffold and the local environment.

Chitosan is one of the most promising biomaterials in tissue engineering because it offers a distinct set of advantageous physico-chemical and biological properties that qualify them for tissue regeneration in various kinds of organs such as skin, bone, cartilage, liver, nerve and blood vessel. Recent studies in regenerative tissue engineering suggest the use of scaffolds to support and organize damaged tissue because three-dimensional matrices provide a more favorable ambient for cellular behavior. Due to their low immunogenic activity, controlled biodegradability and porous structure, chitosan scaffolds are promising materials for the design of tissue engineered systems.

It is known that the microstructure such as pore size, shape and distribution, has prominent influence on cell intrusion, proliferation and function in tissue engineering. Cell attachment studies on the scaffolds showed that higher DD favored cell adhesion (Seda Tigli Karakecili et al. 2007). The present disclosure, however, contemplates chitosan DD from 56% to 99%.

The degradability of a scaffold plays a crucial role on the long-term performance of tissue-engineered cell/material constructs because it affects many cellular processes, including cell growth, tissue regeneration, and host response. If a scaffold is used for tissue engineering of the skeletal system, degradation of the scaffold biomaterial should be relatively slow, as it has to maintain the mechanical strength until tissue regeneration is completed or nearly so. The degradation rate also inherently affects both the mechanical and solubility properties over time.

Recently, attention has been focused on making polymeric nanofibers by electrospinning process as a unique technique because it can produce chitosan nanofibers with diameter in the range from several micrometers down to tens of nanometers, depending on polymer and processing conditions. Electrospinning applies high voltages to a capillary droplet of polymer solution or a melt to overcome liquid surface tension and thus enables the formation of much finer fibers than conventional fiber spinning methods. These nanofibers mimic the structure and function of the natural extracellular matrix (ECM) and are of great interest in tissue engineering as scaffolding materials to restore, maintain or improve the function of human tissue, because they have several useful properties such as high specific surface area and high porosity. The recent attempts have been made to prepare chitosan-based nanofibrous structures by electrospinning, with varying degrees of success. Min et al. (Min, Lee et at. 2004) produced chitin and chitosan nanofibers with an average diameter of 110 nm and their diameters ranged from 40 to 640 nm by the SEM image analysis. Bhattarai et al. (Bhattarai, Edmondson et al. 2005) further concluded that these chitosan-based nanofibers promoted the adhesion of chondrocyte and osteoblast cells and maintained characteristic cell morphology.

Wound Healing

Chitin and chitosan activate immunocytes and inflammatory cells (e.g., PMNs and macrophages), fibroblasts and angio-endothelial cells. These effects are related to the DD of the samples, chitin presenting a weaker effect than chitosan. Okamoto and coworkers reported that chitosan influenced all stages of wound repair in experimental animal models (Okamoto, Shibazaki et at. 1995). In the inflammatory phase, chitosan has unique hemostatic properties that are independent of the normal clotting cascades. In vivo these polymers can also stimulate the proliferation of fibroblasts and modulate the migration behavior of neutrophils and macrophages modifying subsequent repair processes such as fibroplasias and re-epithelialization (Okamoto, Shibazaki et al. 1995; Kosaka, Kaneko et al. 1996). Kosaka et al. reported that the cell binding and cell-activating properties of chitosan play a crucial role in its potential actions. These studies have added further to the body of evidence that chitosan is suitable as a wound healing material where cell-seeding onto chitosan-based scaffolds would provide tissue engineered implant being biocompatible and viable.

Chitosan oligomers have also exhibited wound-healing properties (Minagawa, Okumura et al. 2007). It is suggested that their wound-healing properties are due to their ability to stimulate fibroblast production by affecting the fibroblast growth factor. Subsequent collagen production further facilitates the formation of connective tissue (Howling, Dettmar et al. 2001).

The potential use of chitin oligosaccharides in wound healing as well as their capacity against chronic bowel disease has been studied (Deters, Petereit et al. 2008). The wound healing effect of chitosan oligomers and monomers is of great interest because in vivo lysozyme degrades chitosan polymer to these smaller molecules.

Chitosan-based implants have been found to evoke a minimal foreign body reaction, with le or no fibrous encapsulation. The typical course of healing is with formation of normal granulation tissue, often with accelerated angiogenesis. Chitosan possesses the properties favorable for promoting rapid dermal regeneration and accelerating wound healing suitable for applications extending from simple wound dressings to sophisticated artificial skin matrices. During the course of chitosan implant degradation by macrophage-like cells, the chitosan has been reported to stimulate an anti-inflammatory cytokine cascade (Chellat, Grandjean-Laquerriere et al. 2005).

An ideal cutaneous dressing would control the evaporative water loss from a wound at an optimal rate. The transepidermal water loss (TEWL) rate for normal skin is 204 $g/m^2$ per day, while that for injured skin with a compromised stratum corneum and epidermis can range from 279 $g/m^2$ per day for a "first-degree" burn to 5138 $g/m^2$ per day for a granulating wound lacking the epidermis. The water vapor permeability of a wound dressing should prevent both excessive dehydration as well as buildup of exudate. It was recommended that a rate of 2500 $g/m^2$ per day, which being in the mid-range of loss rates from injured skin, would provide an adequate level of moisture without risking wound dehydration. The water loss data for fabricated asymmetric chitosan membranes ranged from 2109 to 2792 $g/m^2$ per day depending on the per-evaporation time before membrane casting (Mi, Shyu et al. 2001). The high porosity of the sponge-like sublayer increases the adsorption of water vapor and the decreased thickness of dense skin layer increases the diffusion of water molecule, thus resulting in the increased water vapor transmission rate.

Drug Delivery Systems

An important application of chitosans in industry is the development of drug delivery systems such as nanoparticles, hydrogels, microspheres, films and tablets. As a result of its cationic character, chitosan is able to react with polyanions giving rise to polyelectrolyte complexes. Pharmaceutical applications include nasal, ocular, oral, vaginal, parenteral, and transdermal drug delivery. Three main characteristics of chitosan to be considered are: Mw, DD, and purity. When chitosan chains become shorter (low Mw chitosan), they can be dissolved directly in water, which is particularly useful for specific biomedical applications, when pH should stay at around 7.0, or slightly lower (ca. 5.5-6.5) for dermatologic or consumer skincare applications.

In drug delivery, the selection of an ideal type of chitosan with certain characteristics is useful for developing sustained drug delivery systems, prolonging the duration of drug activity, improving therapeutic efficiency and reducing side effects. The physicochemical characteristics of chitosan are important for the selection of the appropriate chitosan as a material for drug delivery vehicles.

The DD controls the degree of crystallinity and hydrophobicity in chitosan due to variations in hydrophobic interactions which control the loading and release characteristics of chitosan matrices (Draget 1996). Zhang et al. also reported that a high chitosan DD and narrow polymer Mw distribution were shown to be critical for the control of particle size distribution (Zhang, Oh et al. 2004).

Desai and Park observed that the release rate of vitamin C was much lower as the Mw of chitosan used for preparing microspheres increased (Desai and Park 2006). They studied the release kinetics and found that it followed Fick's law of diffusion.

With regard to in vitro release studies, the amount of drug released is similar for films that contained low and medium Mw chitosan, but lower for the ones prepared with high Mw chitosan. This behavior is predictable, taking into account the direct relationship between the molar mass of chitosan and the viscosity of its solution. By increasing the viscosity of the polymer, the diffusion of the drug through the formed gel layer into the release medium was retarded (El-Kamel, Ashri et at. 2007).

Gene Delivery

Due to its positive charge, chitosan has the ability to interact with negatively charged molecules such as DNA. This property was used for the first time in 1995 to prepare a non-viral vector for a gene delivery system (MacLaughlin, Mumper et al. 1998). The use of chitosan as non-viral vector for gene delivery offers several advantages compared to viral vectors. Mainly, chitosan does not produce endogenous recombination, oncogenic effects and only mild immunological reactions. Moreover, chitosan/plasmid DNA complexes can be easily prepared at low cost.

The Mw of chitosan is a key parameter in the preparation of chitosan/DNA complexes since transfection efficiency correlates strongly with chitosan Mw. High molecular weight chitosan renders very stable complexes but the transfection efficiency is very low. To improve transfection efficiency, recent studies have examined the use of low Mw chitosans and oligomers in gene delivery vectors. It appears that a fine balance must be achieved between extracellular DNA protection (better with high Mw) versus efficient intracellular unpackaging (better with low Mw) in order to obtain high levels of transfection. Lavertu et al. studied several combinations of Mw and DD of chitosan finding two combinations of high transfection efficiency using a chitosan of 10 kDa and DD of 92 and 80%, respectively (Lavertu, Methot et al. 2006).

Kiang et al, studied the effect of the degree of chitosan deacetylation on the efficiency of gene transfection in chitosan-DNA nanoparticles (Kiang, Wen et al. 2004). Highly deacetylated chitosan (above 80%) releases DNA very slowly. They suggest that the use of chitosan with a DD below 80% may facilitate the release of DNA since it lowers the charge density, may increase steric hindrance in complexing with DNA, and is known to accelerate degradation rate. They reported an increase in luciferase reporter gene expression when the DD was decreased from 90% to 70%. Formulations with 62% and 70% deacetylation led to luciferase transgenic expression two orders of magnitude higher than chitosan with 90% deacetylation.

Chitosan Membranes

A potential and practical use for a chitosan membranes or films is as a barrier membrane to separate tissue layers during surgery. Three methods are typically used to produce membrane-like or film-like chitosan structures of low to high density. These preparation methods are solvent casting, phase separation, and immersion-precipitation phase inversion (Madihally and Matthew 1999; Hong, Wei et al. 2007). For all three methods, chitosan solutions of varying concentrations (e.g., 2-4% w/v) are prepared by dissolving the appropriate amount of chitosan powder (e.g., 75-90% DD/400-500 mPas) in a 1% (v/v) acetic acid solution. Next, the chitosan solution is cast into custom silicone mold cavities. At this point the three different methodologies, described below, diverge one from another.

In the phase separation method, the casted acidic chitosan solution is frozen at $-20°$ C. overnight and then freeze dried at $-40°$ C. at $10 \times 10^{-3}$ mBar for 48 hours. The freeze-dried chitosan material is then de-molded and treated with 1N NaOH for 4 h to stabilize the chitosan polymer network, repeatedly washed with distilled water and then placed in a 50° C. oven for drying. The phase separation method results in a relatively low density porous "sponge" with a pore size that can be controlled (Mi, Shyer et al. 2001) (No et al. 2002).

Freezing of a chitosan solution produces two or more distinct phases—typically water freezing into ice with displacement of the chitosan biomaterial into a separate solid phase. Another step is required to remove the frozen solvent (typically ice), and hence produce the low-density porous sponge, which is a form commonly used in wound dressings. This is accomplished without disturbing the fibrous structure by a freeze-drying (i.e., lyophilization) and/or a freeze substitution step.

For the solvent cast method, the casted acidic chitosan solution is simply dried in an oven at 50° C. to remove the solvent, leaving a chitosan membrane. After drying, the chitosan membranes are treated with 1N NaOH for 4 h, repeatedly washed with distilled water to remove any traces of reacting agents and then placed in an oven at 50° C. for drying. As the solvent starts to vaporize after the solution is cast in this process, the solvent on the surface of the polymer solution vaporizes faster than that of the inside, so the concentration of polymer increases quickly to form the layer shaped by means of the colloid particle. After the forming of the surface layer, vaporizing of the solvent slows down. The chitosan solubility is not enough to maintain the system as a homogeneous solution and results in phase separation. Solvent separating from the homogeneous solution forms a polymer-poor phase surrounded by a polymer-rich phase. The exchange of acidic solvent with neutralizing base stabilizes the polymer network.

In a third approach, the immersion-precipitation phase inversion (IPPI) method, the casted acidic chitosan solution is (partially) dehydrated in an oven at 50° C. for 1 hour to form an asymmetric membrane, subsequently the chitosan polymer in the membrane is stabilized by immersion into a 0.2 M NaOH solution for 24 hours. The resulting membrane is then washed repeatedly with deionized water and then freeze-dried for 48 hours. The IPPI method results in an asymmetric porous membrane with three layers: a dense outer layer, a less dense middle transition layer and then a spongy porous layer, all of which can be controlled (Hong, Wei et al. 2007).

Reviews on chitosan and its uses have been published (Kato, Onishi et al. 2003; Niekraszewicz 2005; Boateng, Matthews et al. 2008; Aranaz, Mengibar et al. 2009; Zhang, Xia et al. 2010).

The making and use of chitosan sponges are described in the prior art:
(1) for uncompressed lyophilized neutralized sponge (Zhang, Cheng et al. 2006; Seda Tigli, Karakecili et al. 2007; Blan and Birla 2008); and
(2) for uncompressed lyophilized non-neutralized sponge (Tully-Dartez, Cardenas et al. 2010; McAdams, Block et al. 2011).

There are several other described methods to increase the density of chitosan materials including:
(1) Compression of a lyophilized acidic sponge to unspecified density (McCarthy, Gregory et al. 2008; Gregory and McCarthy 2009);
(2) Compression of a lyophilized acidic sponge to a specified density less than or equal to 0.8 g/cm3 (McCarthy, Gregory et al. 2008; Gregory and McCarthy 2010; McAdams, Block et al. 2011; McCarthy, Gregory et al. 2011);
(3) Asymmetric air drying (Ma, Wang et al. 2001; Thein-Han and Stevens 2004; Kuo 2005; Kuo, Chang et al. 2006; Dallan, da Luz Moreira et al. 2007; Duan, Park et al. 2007; Hong, Wei et al. 2007; Pang, Chen et al. 2007; Kuo 2008) (Ma et al. 2001) (Duan et al. 2007); and
(4) Electrospinning followed by rolling (Yeo, Jeon et al. 2005; Li and Hsieh 2006; Park, Kang et al. 2006). Electrospinning produces thin, neutralized chitosan fibers that can be blended together in a layered web product. Electrospinning technology does not apply to the present invention described herein.

Chitosan structures can be strengthened by cross-linking chemically with or without the requirement for light activation (Masuoka, Ishihara et al. 2005; Obara, Ishihara et al. 2005). However, none of these cross-linking methods can increase the density of chitosan to the high-density range of the present invention described herein.

Asymmetric air-drying increases the density of a chitosan solution by evaporation of acidic solvent from the exposed surface of the chitosan solution. As the solvent is removed, the density of the chitosan on the exposed surface increases. This method of increasing chitosan density can result in a dense, membrane-like chitosan device. A particular problem with this method is the uneven nature of surface evaporation of a solution within a mold, and the limited density that can be achieved without compression. An additional problem with manufacturing dense chitosan membrane structures by the use of air drying alone is that swelling of the dried membrane upon wetting is excessive and clinically problematic for materials intended as dense and thin barrier membranes. Therefore, unlike the prior art, the present invention describes a novel method of creating a high-density membrane-like chitosan material that circumvents current problems.

SUMMARY

To date, the use of purified chitosan as a barrier membrane or film in surgical and wound healing applications has been limited by the physical properties of chitosan. Chitosan prepared as described in the prior art can result in a film, membrane, or sponge that is of insufficient density or other physical properties for medical use. When wetted to be made pliable, as typically required for medical application, chitosan prepared with a density<0.6 mg/cm$^3$ has insufficient strength to reliably support robust suturing and handling during surgical placement. We have, therefore, developed a novel process to create chitosan membranes of density>0.6 mg/cm$^3$ with additional coincident beneficial properties. This high-density chitosan film or membrane provides the necessary strength and handling qualities to be reliably applied in the clinic. Specifically, the high-density chitosan films or membranes of the present invention have excellent tensile strength, suture retention (i.e., resistance to suture pull-out), elasticity, suitable thickness, and shape memory (i.e., conformability) for use in the medical fields, yet with limited swelling upon rehydration.

Of the several methods known for increasing chitosan density, the most common include compression of a lyophilized chitosan sponge. While the lyophilized chitosan scaffold can be compressed to a high density using sufficient pressure, the limitation of this common procedure is that the compressed lyophilized scaffold retains shape memory upon rewetting and recoils excessively to a clinically unacceptable thickness as a membrane. Limiting the recoil thickness after wetting and maintaining sufficient density in a membranous structure is not possible by this method of compressing a lyophilized sponge, and therefore not suitable for creating a dense membrane with enough strength for clinical handling and suturing. Hence, the present invention describes a new method of creating a dense chitosan membrane of approximately 0.6-1.6 g/cm$^3$ that is less than 2 mm thick and the invention eliminates the common step of sponge fabrication prior to compression.

The essence of the present invention is the making and use of a membranous chitosan material that is denser than a lyophilized chitosan sponge with additional properties such as adequate tensile strength, suture retention (i.e., resistance to suture pull-out), elasticity, and sufficient shape memory (i.e., conformability), yet with limited swelling upon rehydration that is distinct from previously described chitosan materials. The present invention does not restrict the source of chitin or chitosan from natural, semi-synthetic, or synthetic sources.

The key steps of producing the present invention are:

1) Soak an acidic chitosan solution in a strong base until all of the acid in the material is neutralized and the resulting solidified chitosan gel has a basic pH. Air drying prior to neutralization is not excluded by this invention. The use of a mold or form to retain the chitosan solution during said neutralization process is preferable to maintain a desired concentration of chitosan per unit area, preferably approximately 0.3-0.5 g chitosan solution per cm$^2$. Freezing of the chitosan solution in the mold prior to said neutralization is preferable to stabilize the concentration of chitosan per unit area during the neutralization process and to promote polymer exclusion prior to neutralization. A strong base familiar to those practiced in the science of chemistry, preferably sodium hydroxide of 1-2 molarity, is preferred to polymerize the frozen chitosan suspension from the outside of the frozen chitosan suspension towards the inside before chitosan is lost from the surface and the uniform chitosan structure is altered.

2) Remove the water or liquid from the solid chitosan gel while at the same time compressing the chitosan. Dehydration is preferably performed after exchanging the strong base within the solidified chitosan gel with an aqueous buffer or water. Dehydration is preferably performed under vacuum in the presence of heat. Dehydration is preferably performed by loss of the solvent phase (e.g., water, aqueous buffer) through a semipermeable membrane (e.g., Cellophane or a similar cellulosic material), while under vacuum in the presence of heat. Compression is preferably with a minimal linear pressure of 25 inches of Hg dispersed evenly over the chitosan gel.

An important unique aspect of the present invention is combining the processes of compression and dehydration so that dehydration of the gel occurs during compression. Another unique aspect of the invention is the neutral or alkaline pH of the gel during dehydration.

These and other objects, features, and advantages of the present invention may be more clearly understood and appreciated from a review of the following detailed description of the disclosed embodiments and by reference to the appended claims.

DETAILED DESCRIPTION

Based on the foregoing discoveries, there is provided herein a novel chitosan structure having a density of greater than 0.6 g/cm³, methods of making the composition, and methods of using the composition for the medical uses described in the background of this document. The method of making the chitosan structure can be characterized by the following three sequential steps:

a) providing an acidic solution of water and chitosan;
b) neutralizing said solution to form a gel of polymerized chitosan;
c) simultaneously dehydrating and compressing the polymerized chitosan gel.

In a preferred embodiment the resulting high-density chitosan film or membrane composition has a density greater than 0.6 g/cm³, and more preferably greater than 0.8 g/cm³.

In a preferred embodiment of the present invention, the chitosan starting material used in the acidic solution is approximately 70-95% DD. However, the present invention also allows for DD from 56%-99%.

In a preferred embodiment the chitosan is present as chitosan base. However, the chitosan may be present as a salt such as chitosan acetate, chitosan succinate, chitosan adipate, chitosan chloride, chitosan glutamate, chitosan lactate, chitosan aspartate, chitosan pyruvate, chitosan phosphate, chitosan glycolate, chitosan ascorbate, chitosan salicylate, chitosan formate, or chitosan malate.

In another preferred embodiment of the present invention, the chitosan starting material has an average viscosity of approximately 400-500 Centipoise (CPS) or Millipascal (mPas). However, the present invention contemplates chitosan starting material viscosities from about 5 to 3000 mPas.

In a preferred embodiment of the present invention, the chitosan is solubilized in 1% acetic acid. However, the present invention considers acidic solvents other than acetic acid and solvent percentage ranging from 0.1%-10%. For example an appropriate organic acid with pH less than 5.0 such as formic, glycolic, citric, or lactic acid would also be suitable. Other suitable acids include hydrochloric acid, glutamic acid, aspartic acid, ascorbic acid, pyruvic acid, malic acid, maleic acid, fumaric acid, glucuronic acid, sorbic acid, and folic acid.

In a preferred embodiment of the present invention, the chitosan concentration in the solution is 2-4%. However, the present invention contemplates chitosan concentrations of 0.1% to 25%.

In another preferred embodiment of the present invention, the chitosan is solubilized in acidic solvent for 7 days prior to forming a neutralized chitosan gel (either with or without a freezing step prior to neutralization). However, the present invention considers chitosan solutions prepared immediately, or up to 2 years prior to forming the neutralized chitosan gel (either with or without a freezing step prior to neutralization).

In a preferred embodiment of the present invention, the chitosan solution is poured into a form or mold in an amount at a thickness of approximately 0.3-0.5 g chitosan solution per square cm of the form or mold area. However, the present invention contemplates chitosan solution amounts as low as 0.1 g/cm2 or as high as 10 g/cm2 within the mold or form prior to freezing.

In a preferred embodiment of the present invention, the chitosan solution is allowed to degas by applying vibration to the solution through the mold or form. Vibration time is preferably 10 minutes. However, the present invention contemplates vibration times from 1 second to 10 days. In an alternative embodiment, the present invention contemplates degassing the chitosan solution using an applied vacuum.

In a preferred embodiment of the present invention, the chitosan solution is frozen in the mold or form to become a solidified chitosan suspension. In a preferred embodiment of the present invention, the chitosan solution is frozen at approximately −80° C. for 1 h. In an alternative embodiment, the chitosan solution is frozen at approximately −20° C. for 16 h. However, the present invention contemplates freezing of the chitosan solution at temperatures ranging from 0° C. to −276° C. for times ranging from 1 minute to 365 days, sufficient to freeze the chitosan solution. The present invention also contemplates the possibility of not freezing the chitosan solution at this stage of the process.

In a preferred embodiment of the present invention, the solidified (if frozen) chitosan suspension is de-molded (removed from the mold) while solid and subsequently immersed in a base, such as 1-2M sodium hydroxide, while solid, for 24 h to completely neutralize the acidic solvent within the solidified chitosan suspension, producing a polymerized gel. However, the strength and volume of the base required to completely neutralize the acidic solvent within the solidified chitosan gel, and the duration of the immersion, may vary according to the size and acidity of the solidified chitosan suspension. The present invention contemplates any one of several bases known to those practiced in the science of chemistry, such as sodium hydroxide or potassium hydroxide, having a strength ranging from 0.1M to 10M, with an immersion period ranging from 1 minute to 3 months. Alternative hydroxides may be used, and they include calcium hydroxide and magnesium hydroxide.

In a preferred embodiment of the present invention, the neutralized chitosan gel with a basic pH is washed for 24 h in deionized or distilled $H_2O$ or aqueous buffer solution to remove the basic solution to become pH neutral or substantially neutral (e.g. pH 5-11, 5-9 or 5.5-7.5). However, the present invention contemplates a washing period from 1 minute to 3 months. The present invention also contemplates using continuous flow of deionized or distilled $H_2O$ or aqueous buffer solution during this rinsing step. The present invention also contemplates not washing the neutralized chitosan gel at all.

In a critical aspect of the present invention, the liquid is removed from the neutralized chitosan gel while concurrently compressing the chitosan. Dehydration is preferably performed with the use of a vacuum and heat. Compression is preferably performed with a minimal linear pressure of 25 inches of Hg and is preferably dispersed evenly over the chitosan gel to obtain a uniform membrane. However, compression is contemplated using a minimal linear pressure of 5-500, 10 to 100, or 20 to 50 inches of Hg. Dehydration and compression are preferably performed at a temperature of 80° C. However, the present invention contemplates dehydrating and compressing the chitosan gel at temperatures ranging from 2° C. to 150° C., 40° to 120° C., or 50° to 100° C.

Of course, it will be understood that dehydration and physical compression can occur in the presence of a vacuum, either by itself or with added heat, in a process known as outgassing.

The vacuum applied is preferably less than atmospheric pressure, and as low as 0.6, 0.4 or 0.2 atmospheres.

Dehydration and compression are preferably performed for a period of 4 hours. However, the present invention contemplates the performance of dehydration and compression for periods of time ranging from 1 minute to 3 months.

In a preferred embodiment of the present invention, the neutralized chitosan gel is placed on or inside a semi-permeable membrane, prior to application of vacuum dehydration. The semi-permeable membrane subsequently facilitates loss of water vapor under vacuum, while preserving the integrity of the dehydrating and dehydrated polymeric chitosan. The semi-permeable membrane is selectively permeable for water, while retaining the molded chitosan gel within the margins or boundaries of the semi-permeable membrane, and may be a Cellophane or other cellulosic membrane or another material. The dehydrated high-density chitosan film or membrane may be subsequently removed from the semi-permeable membrane used during the dehydration process.

In another preferred embodiment of the present invention, the neutralized and polymerized chitosan gel is immersed in a glycerol solution for a period of time ranging from 1 second to 10 days, then placed on or inside a semi-permeable membrane for vacuum dehydration. Furthermore, it is preferred that the glycerol solution contains approximately 5% to 20% or 10% glycerol in water or in aqueous buffer. However, the present invention may use glycerol concentrations ranging from 1% to 50% during this process.

The resulting chitosan structure preferably takes the form of a film or membrane having a thickness less than 10 mm, 5 mm, 2 mm, 1 mm, or even 0.5 mm. The density of the structure, as noted previously, preferably exceeds $0.6 \text{ g/cm}^3$, and may be up to $1.6 \text{ g/cm}^3$. In another preferred embodiment the density of the structure exceeds $0.8 \text{ g/cm}^3$, and may be up to $1.6 \text{ g/cm}^3$. The film or membrane can also be characterized by its pH, which preferably ranges from 5.0 to 9.5. The film or membrane can be chopped up or ground and used as particulates, but is preferably used as a film or membrane due to its excellent physical properties (e.g., tensile strength, elasticity, and resistance to suture pull-out).

In a preferred embodiment the chitosan film or membrane of this invention does not require a chemical or light-induced cross-linking step, and yet attains a dehydrated density of $>0.6 \text{ g/cm}^3$ and more preferably $>0.8 \text{ g/cm}^3$. However, for some applications the inclusion of a chemical or light-induced cross-linking step might provide some benefit(s), such as reduced biodegradation potential.

In another embodiment, the resulting dense chitosan structures of the present invention have physical properties that are beneficial for use in biomedical procedures in an animal, mammal, or human, such as surgically implanted films or membranes. When assessed for tensile strength, elasticity, and/or resistance to suture pull-out, the dense chitosan materials demonstrate excellent physical characteristics. ASTM International standard methods have been established for the evaluation of these physical parameters for thin films or membranes (ASTM 2002; ASTM 2006). These standard methodologies with minor modifications (e.g., for tensile testing strips semi-circular rather than semi-oval template cut-outs according to ASTM standard method. D 1708-06a, and having a minimum width of ~2.5 mm (ASTM 2006); for suture pull-out strips having a width of ~5 mm) have been utilized to characterize the resulting dense chitosan structures of the present invention.

The present invention discloses a composition comprising chitosan in a film or membrane having a density greater than $0.6 \text{ g/cm}^3$, and more preferably greater than $0.8 \text{ g/cm}^3$. In another preferred embodiment the chitosan composition has a pH of from 5.0 to 9.5. In another preferred embodiment the chitosan composition includes glycerol.

Finally, the invention provides methods of treatment using the structures of the present invention, and can thus be defined as a method of treatment comprising: providing a chitosan composition having a density greater than $0.6 \text{ g/cm}^3$; and placing said composition on or within an animal. In preferred embodiments the animal is a mammal or human, and in another preferred embodiment the structure is hydrated in water or a buffered aqueous solution and in the presence or absence of one or more compounds selected from a pharmaceutical, a biologic agent, a nucleic acid, a vaccine, an immune effector, or a salt thereof prior to use. In another preferred embodiment the chitosan composition serves as a physical barrier film or membrane to separate tissue layers within an animal. In another preferred embodiment the film or membrane on or within the animal, mammal, or human resorbs over time, and the rate thereof is in part dependent upon the DD and thickness of the material. In another preferred embodiment the chitosan composition serves as an anti-infective physical barrier film or membrane on or within an animal. In another preferred embodiment of the present invention, the chitosan film or membrane is permeable to small molecules in water or aqueous solution. In another preferred embodiment of the present invention, the physical properties (e.g., tensile strength, elasticity, and resistance to suture pull-out) alone or in addition to clinical handling characteristics (e.g., wet-ability, conformability to surgical implant sites, and suture-ability) facilitate excellent ease-of-use of the resulting dense chitosan films or membranes in clinical settings in an animal, mammal, or human.

EXAMPLES

In the preferred method of freezing the chitosan solution prior to neutralization, ultra-freezing a chitosan solution of approximately $0.3\text{-}0.5 \text{ g/cm}^2$ in the mold at $-80°$ C. for an hour ultimately results in polymerization of the chitosan on the exposed top surface with a woven, fibrillar, porous, structure at that surface when examined by microscopy or scanning electron microscopy. The resulting dehydrated film or membrane has an overall density $>0.6 \text{ g/cm}^3$ and more preferably $>0.8 \text{ g/cm}^3$ and is somewhat asymmetric, with a smoother, less fibrilar surface on the alternate, bottom side.

In the preferred method of freezing the chitosan solution prior to neutralization, ultra-freezing at $-80°$ C. for significantly more than an hour (e.g., two hours) can result in physical cracking of the frozen chitosan gel and of the final membrane structure.

In the preferred method of freezing, the freezing of the chitosan solution within the mold at $-20°$ C. prior to neutralization, reduces the extent of woven structure of the final membrane structure. Regardless of freezing temperature, the resulting membrane has a density $>0.6 \text{ g/cm}^3$.

In the absence of freezing the chitosan solution prior to neutralization, the resulting compressed and dehydrated membrane has no visible woven, fibrillar structure. Regardless of freezing or lack thereof, the resulting membrane has a density $>0.6 \text{ g/cm}^3$.

The relevance of freezing the acidic chitosan solution prior to neutralization of the acid and dehydration with compression is further exemplified by mechanical properties of the materials generated with and without the freezing process. In measuring the resistance to suture pull-out using an Instron machine, chitosan membranes prepared without the freezing process had an inferior pull-out force of $2.0 \text{ N} \pm 0.3 \text{ N/mm}$ of membrane thickness, while membranes of the same composition prepared with a freezing temperature of −80° C. for 1 h prior to neutralization had a superior resistance to suture pull-out of 4.5 N±0.1 N/mm of membrane thickness.

Exemplifying the importance of neutralizing the frozen chitosan suspension with alkali to a semi-solid gel prior to dehydration and compression, attempts at evaporating while compressing acidic chitosan solutions have failed. Dehydration with compression requires a semipermeable membrane (e.g., Cellophane) to retain the solute (chitosan polymers) while allowing passage of the solvent with a gradual increase in the density of the chitosan while drying. A plausible reason for the inability to dehydrate an acidic chitosan solution through a semi-permeable membrane is that the viscous unpolymerized chitosan eventually accumulates at the surface of the membrane and blocks the passage of the solvent. The result is failure to dehydrate the solution, even in the presence of heat. For the same reasons, freezing of the acidic chitosan solution immediately followed by dehydration and compression also fails. For the same reasons, dehydration with compression of a wet acidic chitosan sponge (produced by lyophilizing the acidic chitosan suspension) also fails, failing to dry with vacuum dehydration. For the same reasons, dehydration with compression of a wet, acidic air-dried chitosan structure also fails. Polymerization of the chitosan suspension by neutralization in alkalai prior to vacuum compression is essential.

Exemplifying the importance of evaporating and compressing a neutralized chitosan gel, attempts at compressing a dry lyophilized acidic sponge resulted in a cracked chitosan membrane structure. Wetting the dry compressed membrane results in unacceptable recoil swelling and loss of the unpolymerized membrane structure.

The importance of maintaining a pH greater than 5.0 following polymerization of the chitosan solution in a strong base into a gel is exemplified by the loss of chitosan gel structure when the neutralized chitosan gel is placed in an acidic solution pH 2.9 for 20 h resulting in disintegration of the chitosan gel structure.

The importance of maintaining a pH environment greater than pH 5.0 following dehydration of the neutralized chitosan gel is exemplified by the complete loss of dense chitosan film or membrane structure following 24 h in an acidic environment of pH 4 or less.

Exemplifying the importance of dehydrating and compressing a neutralized chitosan gel and not a lyophilized sponge, compression of a wetted neutralized lyophilized chitosan sponge results in insufficient chitosan density of 0.38 g/cm$^3$. Compression of a dry neutralized lyophilized chitosan sponge results in insufficient chitosan density (0.065 g/cm$^3$).

Exemplifying the importance of dehydration with compression, concomitantly, experiments where compression was provided in the absence of adequate dehydration during the compression resulted in a fissured and unsatisfactory chitosan final structure.

The effect of vibration on the acidic chitosan solution prior to neutralizing has no effect on final membrane structure.

Exemplifying the biological relevance of chitosan films or membranes with high density, these membranes demonstrated permeability to small molecules. For instance, high density chitosan films or membranes prepared from 4% chitosan solution were permeable to methylene blue and crystal violet (Mw 285 and 373, respectively) in phosphate buffered saline (PBS) solution using Franz cell technology. This demonstrates that the films or membranes are permeable to selected small molecules. Permeability to nutrients on or within an animal, mammal, or human may have physiologic benefits.

Further exemplifying the biological relevance of chitosan films or membranes with high density, living mammalian cells were seeded and maintained on the membranes for at least 3 days in culture. Cell binding and cell compatibility were observed on both sides of the membrane. Evidence of proliferation and cell migration were also demonstrated. Keratinocyte migration was most evident on the smoother surface bottom side while in the mold) relative to the more porous surface (i.e., top side while in the mold) as measured by microscopic image analysis. These results provide evidence of in vitro biocompatibility.

Further exemplifying the biological relevance of chitosan films or membranes with high density, wound healing in a mammalian model was observed when the membranes were surgically placed at the base of full-thickness surgically-induced ulcers of the oral palate in rats. Healing was associated with re-development of collagen in the subepithelial matrix and re-epithelialization of the ulcers. Histological analysis after membrane implantation for 1 to 12 weeks also indicated that the high-density chitosan is biocompatible, while biodegradable or resorbable. Establishment of a physical barrier on or within an animal, mammal, or human that is resorbed over time has clinical utility. For instance a physical barrier between dissimilar tissues (e.g., bone vs. soft tissue) can facilitate differential rates of healing on the opposite sides of the film or membrane. Furthermore, in view of in vitro enzymatic degradation rates, the rates of resorption in vivo (see below) are similarly anticipated to be dependent upon the percentage of DD and/or thickness of dense chitosan films or membranes. In other words, the rates of degradation can be "controlled" at least in part by varying the percentage of DD and/or thickness.

Exemplifying the relevance of density to clinical functionality and utility is the strong correlation between densities of dry chitosan films or membranes and other physical properties, such as tensile strength. The ASTM standard methods with minor modifications (e.g., for tensile testing strips semi-circular rather than semi-oval template cut-outs according to ASTM standard method D 1708-06a, and having a minimum width of ~2.5 mm (ASTM 2006); for suture pull-out strips having a width of ~5 mm) have been utilized to characterize the resulting dense chitosan films or membranes. The dense chitosan films or membranes produced by the methods claimed herein show a direct correlation between membrane density and tensile strength. In general the dense chitosan films or membranes of the present invention when tested with an array of experimental variables from production batch to batch (e.g., amount of starting chitosan solution, dry membrane thicknesses of less than 1 mm and typically 0.2 to 0.6 mm, percentage of DD from 70% to 95%, source materials from different vendors, post-drying process modifications if any, etc.) yield in tests using an Instron machine the following typical ranges of physical properties: (a) maximum tensile load of approximately 2 to 14 N (~2.5 mm minimum width); (b) maximum tensile stress of approximately 20 to 140 MPa (~2.5 mm minimum width); and (c) suture pull-out maximum load of approximately 0.5 to 4.5 N (~5 mm width).

Furthermore exemplifying the relevance of physical characteristics of dense chitosan films or membranes of the present invention to clinical utility is the combination of density, tensile strength, elasticity, and resistance to suture pull-out, some or all of which are desirable features for suture-able implantable surgical membranes.

Exemplifying the relevance of chitosan deacetylation pertaining to the methods disclosed and claimed herein, degradation in a concentrated lysozyme solution buffered at pH 6.5 and 37° C., was complete within 8 days for a 70% DD membrane, complete within 11 days for a 75% DD membrane, partially complete within 18 days for 80% and 85% DD membranes, and not evident in 90% and 95% membranes after 3 weeks under these conditions. These results indicate that the inherent susceptibilities of the starting polymeric materials (i.e. chitosan powder of varying percentage of DD) to enzymatic degradation in vitro have not been destroyed by the processes of the present invention while producing dense chitosan films or membranes. Furthermore, dense chitosan films or membranes of the present invention remain labile to acid depolymerization (and solubilization) without enzymatic degradation when placed in acetic acid solution or a buffered solution at or below pH 4.

Exemplifying the relevance of treating the neutralized and polymerized chitosan gel with a glycerol solution (e.g., 10 or 50 percent glycerol in water) prior to the dehydration step, the resulting film or membrane has high density similar to film or membrane produced without this glycerol solution step, and with beneficial high tensile strength, resistance to suture pull-out, and handling characteristics, for instance flexibility and ease of cutting. This combination of attributes (i.e., physical properties and clinical handling characteristics) provide a film or membrane material of great utility for use on or in an animal, mammal, or human.

Throughout this application, various publications are referenced. The disclosures of these publications are hereby incorporated by reference in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Abou-Shoer, M. (2010). "A Simple Colorimetric Method for the Evaluation of Chitosan." *American Journal of Analytical Chemistry* 01(02): 91-94.

Aimin, C., H. Chunlin, et al. (1999). "Antibiotic loaded chitosan bar. An in vitro, in vivo study of a possible treatment for osteomyelitis." *Clinical Orthopaedics and Related Research* (366): 239-247.

Aranaz, I., M. Mengibar, et al. (2009). "Functional Characterization of Chitin and Chitosan." *Current Chemical Biology* 3: 203-230.

ASTM (2002). "Standard Guide for Characterization and Testing of Biomaterial Scaffolds Used in Tissue-Engineered Medical Products." *ASTM International* F 2150-02.

ASTM (2006). "Standard Test Method for Tensile Properties of Plastics by Use of Microtensile Specimens." *ASTM International* D 1708-06a.

Baldrick, P. (2010). "The safety of chitosan as a pharmaceutical excipient." *Regulatory toxicology and pharmacology* 56(3): 290-299.

Bhattarai, N., D. Edmondson, et al. (2005). "Electrospun chitosan-based nanofibers and their cellular compatibility." *Biomaterials* 26(31): 6176-6184.

Blan, N. R. and R. K. Birla (2008). "Design and fabrication of heart muscle using scaffold-based tissue engineering." *Journal of biomedical materials research. Part A* 86(1): 195-208.

Boateng, J. S., K. H. Matthews, et al. (2008). "Wound healing dressings and drug delivery systems: A review." *Journal of Pharmaceutical Sciences* 97(8): 2892-2923.

Chellat, F., A. Grandjean-Laquerriere, et al. (2005). "Metalloproteinase and cytokine production by THP-1 macrophages following exposure to chitosan-DNA nanoparticles." *Biomaterials* 26(9): 961-970.

Chen, R. and H. Hwa (1996). "Effect of molecular weight of chitosan with the same degree of deacetylation on the thermal, mechanical, and permeability properties of the prepared membrane." *Carbohydrate Polymers* 29: 353-358.

Chow, K. S. and E. Khor (2000). "Novel fabrication of open-pore chitin matrixes." *Biomacromolecules* 1(1): 61-67.

Dallan, P. R. M., P. da Luz Moreira, et al. (2007). "Effects of chitosan solution concentration and incorporation of chitin and glycerol on dense chitosan membrane properties." *Journal of Biomedical Materials Research Part A* 80B(2): 394-405.

Desai, K. G. and H. J. Park (2006). "Effect of manufacturing parameters on the characteristics of vitamin C encapsulated tripolyphosphate-chitosan microspheres prepared by spray-drying." *Journal of Microencapsulation* 23(1): 91-103.

Deters, A., F. Petereit, et al. (2008). "N-Acetyl-D-glucosamine oligosaccharides induce mucin secretion from colonic tissue and induce differentiation of human keratinocytes." *The Journal of Pharmacy and Pharmacology* 60(2): 197-204.

Draget, K. I. (1996). "Association phenomenon in highly acetylated chitosan gels." *Polymer Gels and Networks* 4: 143-151.

Duan, J., S. I. Park, et al. (2007). "Antimicrobial Chitosan-Lysozyme (CL) Films and Coatings for Enhancing Microbial Safety of Mozzarella Cheese." *Journal of Food Science* 72(9): M355-M362.

El-Kamel, A. H., L. Y. Ashri, et al. (2007). "Micromatricial metronidazole benzoate film as a local mucoadhesive delivery system for treatment of periodontal diseases." *AAPS Pharm. Sci. Tech.* 8(3): E75.

Gregory, K. and S. McCarthy (2009). Wound dressings and method for controlling severe, life-threatening bleeding. USPTO. U.S. Pat. No. 7,482,503.

Gregory, K. and S. McCarthy (2010). Wound dressings, apparatus, and methods for controlling severe, life-threatening bleeding. USPTO. U.S. Pat. No. 7,820,872.

He, P., S. S. Davis, et al. (1998). "In vitro evaluation of the mucoadhesive properties of chitosan microspheres." *International Journal of Pharmaceutics* 166(1): 75-88.

Hong, H., J. Wei, et al. (2007). "Development of asymmetric gradational-changed porous chitosan membrane for guided periodontal tissue regeneration." *Composites Part B: Engineering* 38(3): 311-316.

Horton, D. and D. Lineback (1965). N-deacetylation, chitosan from chitin. *Methods in Carbohydrate Chemistry*. R. Whistler and M. Wolfson. New York: 403.

Howling, G. I., P. W. Dettmar, et al. (2001). "The effect of chitin and chitosan on the proliferation of human skin fibroblasts and keratinocytes in vitro." *Biomaterials* 22(22): 2959-2966.

Illum, L. (1998). "Chitosan and its use as a pharmaceutical excipient." *Pharmaceutical research* 15(9): 1326-1331.

Ishihara, M., K. Obara, et al. (2006). "Chitosan hydrogel as a drug delivery carrier to control angiogenesis." *Journal of Artificial Organs: the official journal of the Japanese Society for Artificial Organs* 9(1): 8-16.

Jian, Y., T. Feng, et al. (2008). "Effect of Chitosan Molecular Weight and Deacetylation Degree on Hemostasis." *J. Biomed. Mater. Res. B* 84B: 131-137.

Johnson, E. and E. Nichols (2000). High Tap Density Chitosan, and Methods of Production. USPTO. U.S. Pat. No. 6,130,321: 1-12.

Jou, C. H., L. Yuan, et al. (2007). "Biocompatibility and antibacterial activity of chitosan and hyaluronic acid immobilized polyester fibers." *Journal of Applied Polymer Science* 104: 220-225.

Kato, Y., H. Onishi, et al. (2003). "Application of chitin and chitosan derivatives in the pharmaceutical field." *Current Pharmaceutical Biotechnology* 4(5): 303-309.

Kiang, T., J. Wen, et al. (2004). "The effect of the degree of chitosan deacetylation on the efficiency of gene transfection." *Biomaterials* 25(22): 5293-5301.

Kim, I., S. Seo, et al. (2008). "Chitosan and its derivatives for tissue engineering applications." *Biotechnology Advances* 26(1): 1-21.

Kofuji, K., C. Qian, et al. (2005). "Relationship between physiochemical characteristics and functional properties of chitosan." *European Polymer Journal* 41(11): 2784-2791.

Kosaka, T., Y. Kaneko, et al. (1996). "Effect of chitosan implantation on activation of canine macrophages and polymorphonuclear cells after surgical stress." *The Journal of Veterinary Medical Science: the Japanese Society of Veterinary Science* 58(10): 963-967.

Kuo (2005). "Evaluation of Alginate Coated Chitosan Membrane for Guided Tissue Regeneration." *27th IEEE EMBS Annual International Conference*: 1-4.

Kuo (2008). "Guided tissue regeneration with use of [beta]-TCP/chitosan composite membrane." *Journal of Applied Polymer Science*: 1-8.

Kuo, S. M., S. J. Chang, et al. (2006). "Guided tissue regeneration for using a chitosan membrane: an experimental study in rats." *Journal of biomedical materials research. Part A* 76(2): 408-415.

Langer, R. and J. P. Vacanti (1993). "Tissue engineering." *Science* 260(5110): 920-926.

Lavertu, M., S. Methot, et al. (2006). "High efficiency gene transfer using chitosan/DNA nanoparticles with specific combinations of molecular weight and degree of deacetylation." *Biomaterials* 27(27): 4815-4824.

Lehr, C. M., J. A. Bouwstra, et al. (1992). "In vitro evaluation of mucoadhesive properties of chitosan and some other natural polymers." *International Journal of Pharmaceutics* 78: 43-48.

Li, L. and Y. Hsieh (2006). "Chitosan bicomponent nanofibers and nanoporous fibers." *Carbohydrate Research* 341(3): 374-381.

Lim, S. M., D. K. Song, et al. (2008). "In vitro and in vivo degradation behavior of acetylated chitosan porous beads." *Journal of Biomaterials Science: Polymer Edition* 19(4): 453-466.

Liu, A., Y. Guan, et al. (2001). "Antibacterial action of chitosan and carboxymethylated chitosan." *Journal of Applied Polymer Science* 79: 1324-1335.

Ma, J., H. Wang, et al. (2001). "A preliminary in vitro study on the fabrication and tissue engineering applications of a novel chitosan bilayer material as a scaffold of human neofetal dermal fibroblasts." *Biomaterials* 22(4): 331-336.

MacLaughlin, F. C., R. J. Mumper, et al. (1998). "Chitosan and depolymerized chitosan oligomers as condensing carriers for in vivo plasmid delivery." *Journal of Controlled Release: official journal of the Controlled Release Society* 56(1-3): 259-272.

Madihally, S. V. and H. W. Matthew (1999). "Porous chitosan scaffolds for tissue engineering." *Biomaterials* 20(12): 1133-1142.

Masuoka, K., M. Ishihara, et al. (2005). "The interaction of chitosan with fibroblast growth factor-2 and its protection from inactivation." *Biomaterials* 26(16): 3277-3284.

McAdams, S., W. Block, et al. (2011). Compositions, Assemblies, and Methods Applied During or After a Dental Procedure to Ameliorate Fluid Loss and/or Promote Healing, Using a Hydrophillic Polymer Sponge Structure such as Chitosan. USPTO. U.S. Pat. No. 7,897,832: 1-25.

McCarthy, S., K. Gregory, et al. (2008). Wound dressings and method for controlling severe, life-threatening bleeding. USPTO. U.S. Pat. No. 7,371,403.

McCarthy, S., K. Gregory, et al. (2011). Wound dressing and method for controlling severe, life-threatening bleeding. USPTO. US20110034410A1.

Mi, F. L., S. S. Shyu, et al. (2001). "Fabrication and characterization of a sponge-like asymmetric chitosan membrane as a wound dressing." *Biomaterials* 22(2): 165-173.

Min, B. M., S. W. Lee, et al. (2004). "Chitin and chitosan nanofibers: electrospinning of chitin and deacetylation of chitin nanofibers." *Polymer* 45: 7137-7142.

Minagawa, T., Y. Okamura, et al. (2007). "Effects of molecular weight and deacetylation degree of chitin/chitosan on wound healing." *Carbohydrate Polymers* 67: 640-644.

Muzzarelli, R. A. (2010). "Chitins and chitosans as immunoadjuvants and non-allergenic drug carriers." *Marine Drugs* 8(2): 292-312.

Niekraszewicz, A. (2005). "Chitosan Medical Dressings." *Fibres and Textiles in Eastern Europe* 13: 16-18.

No, H. K., N. Y. Park, et al. (2002). "Antibacterial activity of chitosans and chitosan oligomers with different molecular weights." *Int. J. Food Microbiol.* 74(1-2): 65-72.

Obara, K., M. Ishihara, et al. (2005). "Acceleration of wound healing in healing-impaired db/db mice with a photocrosslinkable chitosan hydrogel containing fibroblast growth factor-2." *Wound repair and regeneration: official publication of the Wound Healing Society [and] the European Tissue Repair Society* 13(4): 390-397.

Okamoto, Y., K. Shibazaki, et al. (1995). "Evaluation of chitin and chitosan on open would healing in dogs." *The Journal of Veterinary Medical Science: the Japanese Society of Veterinary Science* 57(5): 851-854.

Osterballe, M., T. K. Hansen, et al. (2005). "The prevalence of food hypersensitivity in an unselected population of children and adults." *Pediatric Allergy and Immunology: official publication of the European Society of Pediatric Allergy and Immunology* 16(7): 567-573

Osterballe, M., C. G. Mortz, et al. (2009). "The prevalence of food hypersensitivity in young adults." *Pediatric Allergy and Immunology: official publication of the European Society of Pediatric Allergy and Immunology* 20(7): 686-692.

Pang, H. T., X. G. Chen, et al. (2007). "Preparation and function of composite asymmetric chitosan/CM-chitosan membrane." *Journal of Materials Science: Materials in Medicine* 19(3): 1413-1417.

Park, K. E., H. K. Kang, et al. (2006). "Biomimetic nanofibrous scaffolds: preparation and characterization of PGA/chitin blend nanofibers." *Biomacromolecules* 7(2): 635-643.

Park, P. J., J. Y. Je, et al. (2004). "Free radical scavenging activities of differently deacetylated chitosans using an ESR spectrometer." *Carbohydrate Polymers* 55(1): 17-22.

Peng, C. F. (1998). "Synthesis of crosslinked chitosan-crown ethers and evaluation of these products as adsorbents for metal ions." *Journal of Applied Polymer Science* 70: 501-506.

Prashanth, R. and R. Tharanathan (2007). "Chitin/chitosan: Modifications and their unlimited application potential—an overview." *Trends in Food Science Technology* 18: 117-131.

Roberts, G. (1998). *Chitin Chemistry*. London, Macmillan.

Roberts, G. (1998). *Chitosan production routes and their role in determining the structure and properties of the product*. Lyon, Jacques Andre'.

Roldo, M., M. Hornof, et al. (2004). "Mucoadhesive thiolated chitosans as platforms for oral controlled drug delivery: synthesis and in vitro evaluation." *European Journal of Pharmaceutics and Biopharmaceutics: official journal of Arbeitsgemeinschaft fur Pharmazeutische Verfahrenstechnik e. V* 57(1): 115-121.

Schipper, N. G., K. M. Varum, et al. (1996). "Chitosans as absorption enhancers for poorly absorbable drugs. 1: Influence of molecular weight and degree of acetylation on drug transport across human intestinal epithelial (Caco-2) cells." *Pharmaceutical Research* 13(11): 1686-1692.

Seda Tigli, R., A. Karakecili, et al. (2007). "In vitro characterization of chitosan scaffolds: influence of composition and deacetylation degree." *Journal of Materials Science: Materials in Medicine* 18(9): 1665-1674.

Smith, T. (1994). Rigid Materials Having High Surface Area and Low Density. USPTO. U.S. Pat. No. 5,328,939.

Thein-Han, W. W. and W. F. Stevens (2004). "Transdermal delivery controlled by a chitosan membrane." *Drug Development and Industrial Pharmacy* 30(4): 397-404.

Tigli, R. and M. Gumusderelioglu (2008). "Evaluation of RGD- or EGF-immobilized chitosan scaffolds for chondrogenic activity." *International Journal of Biological Macromolecules* 43(2): 121-128.

Tully-Dartez, S., H. E. Cardenas, et al. (2010). "Pore Characteristics of Chitosan Scaffolds Studied by Electrochemical Impedance Spectroscopy." *Tissue Engineering; Part C* 16: 339-345.

Unger, P. and R. Rohrbach (1996). Highly Porous Chitosan Bodies. USPTO. U.S. Pat. No. 5,525,710: 1-9.

Yeo, Y.-J., D.-W. Jeon, et al. (2005). "Effects of chitosan nonwoven membrane on periodontal healing of surgically created one-wall intrabony defects in beagle dogs." *Journal of Biomedical Materials Research Part B: Applied Biomaterials* 72(1): 86-93.

Zhang, H., M. Oh, et al. (2004). "Monodisperse chitosan nanoparticles for mucosal drug delivery." *Biomacromolecules* 5(6): 2461-2468.

Zhang, J., W. Xia, et al. (2010). "Chitosan Modification and Pharmaceutical/Biomedical Applications." *Marine Drugs* 8(7): 1962-1987.

Zhang, Y., X. Cheng, et al. (2006). "Novel chitosan/collagen scaffold containing transforming growth factor-β1 DNA for periodontal tissue engineering." *Biochemical and Biophysical Research Communications* 344(1): 362-369.

We claim:

1. A method of producing a chitosan composition with a density greater than 0.6 g/cm3 comprising in sequence:
   a) providing an acidic solution of water and chitosan;
   b) neutralizing said solution to form a polymerized gel; and
   c) simultaneously dehydrating and compressing the gel;
      further comprising freezing said acidic solution prior to neutralizing step (b).

2. The method of claim 1 further comprising washing said gel in water or a buffered aqueous solution prior to dehydrating step (c).

3. The method of claim 1 further comprising washing said gel in water or a buffered solution to a pH of from 5.5 to 7.5 prior to dehydrating step (c).

* * * * *